(12) United States Patent
Keefe et al.

(10) Patent No.: US 10,307,596 B2
(45) Date of Patent: *Jun. 4, 2019

(54) ANTITACHYCARDIA PACING PULSE FROM A SUBCUTANEOUS DEFIBRILLATOR

(71) Applicant: CAMERON HEALTH, INC., St. Paul, MN (US)

(72) Inventors: James M. Keefe, Penn Valley, PA (US); Rick Sanghera, San Clemente, CA (US)

(73) Assignee: Cameron Health, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/817,940

(22) Filed: Nov. 20, 2017

(65) Prior Publication Data

US 2018/0071531 A1 Mar. 15, 2018

Related U.S. Application Data

(63) Continuation of application No. 13/491,492, filed on Jun. 7, 2012, now Pat. No. 9,849,291.

(Continued)

(51) Int. Cl.
*A61N 1/00* (2006.01)
*A61N 1/362* (2006.01)
(Continued)

(52) U.S. Cl.
CPC ......... *A61N 1/3622* (2013.01); *A61N 1/3962* (2013.01); *A61N 1/0504* (2013.01); *A61N 1/3756* (2013.01)

(58) Field of Classification Search
CPC .. A61N 1/3622; A61N 1/3962; A61N 1/0504; A61N 1/3756
See application file for complete search history.

(56) References Cited

U.S. PATENT DOCUMENTS

| 5,366,487 A | 11/1994 | Adams et al. |
|---|---|---|
| 6,647,292 B1 | 11/2003 | Bardy et al. |

(Continued)

FOREIGN PATENT DOCUMENTS

| EP | 0560569 A2 | 9/1993 |
|---|---|---|
| WO | 9319809 A1 | 10/1993 |
| WO | 2012170868 A1 | 12/2012 |

OTHER PUBLICATIONS

Ratner et al., "Terminating ventricular tachyarrhythmias using far-field low-voltage stimuli: Mechanisms and delivery protocols", Heart Rhythm, 10(8)1209-1217, Aug. 2013.

(Continued)

*Primary Examiner* — Lindsey G Wehrheim
(74) *Attorney, Agent, or Firm* — Seager, Tufte & Wickhem LLP

(57) ABSTRACT

Devices and methods for single therapy pulse (STP) therapy for tacharrythmia are disclosed. The STP therapy can be delivered from a far-field position to allow a "global" capture approach to pacing. Due to the global capture in STP, a series of pulses, which is indicative of conventional anti-tachycardia pacing (ATP) delivered by transvenous systems, becomes unnecessary. One to four pulses at most are needed for STP, and after delivery of the one to four pulses, therapy delivery can be interrupted to determine whether the previously delivered therapy has been successful.

20 Claims, 5 Drawing Sheets

Related U.S. Application Data

(60) Provisional application No. 61/605,145, filed on Feb. 29, 2012, provisional application No. 61/495,114, filed on Jun. 9, 2011.

(51) Int. Cl.
*A61N 1/39* (2006.01)
*A61N 1/05* (2006.01)
*A61N 1/375* (2006.01)

(56) References Cited

U.S. PATENT DOCUMENTS

| | | | |
|---|---|---|---|
| 6,721,597 | B1 | 4/2004 | Bardy et al. |
| 6,754,528 | B2 | 6/2004 | Bardy et al. |
| 6,856,835 | B2 | 2/2005 | Bardy et al. |
| 6,865,417 | B2 | 3/2005 | Rissmann et al. |
| 6,937,907 | B2 | 8/2005 | Bardy et al. |
| 6,952,608 | B2 | 10/2005 | Ostroff |
| 6,952,610 | B2 | 10/2005 | Ostroff et al. |
| 6,954,670 | B2 | 10/2005 | Ostroff |
| 7,065,407 | B2 | 6/2006 | Bardy et al. |
| 7,120,495 | B2 | 10/2006 | Bardy et al. |
| 7,149,575 | B2 | 12/2006 | Ostroff et al. |
| 7,194,302 | B2 | 3/2007 | Bardy et al. |
| 7,248,921 | B2 | 7/2007 | Palreddy et al. |
| 7,330,757 | B2 | 2/2008 | Ostroff et al. |
| 7,359,754 | B2 | 4/2008 | Bardy et al. |
| 7,376,458 | B2 | 5/2008 | Palreddy et al. |
| 7,392,085 | B2 | 6/2008 | Warren et al. |
| 7,477,935 | B2 | 1/2009 | Palreddy et al. |
| 7,555,338 | B2 | 6/2009 | Ostroff |
| 7,623,909 | B2 | 11/2009 | Sanghera et al. |
| 7,623,913 | B2 | 11/2009 | Phillips |
| 7,623,916 | B2 | 11/2009 | Julian |
| 7,655,014 | B2 | 2/2010 | Ko et al. |
| 7,751,887 | B1 | 7/2010 | Kroll et al. |
| 7,769,457 | B2 | 8/2010 | Fonte |
| 7,962,212 | B2 | 6/2011 | Signoff et al. |
| 8,079,959 | B2 | 12/2011 | Sanghera et al. |
| 8,160,686 | B2 | 4/2012 | Allavatam et al. |
| 8,160,687 | B2 | 4/2012 | Warren et al. |
| 8,509,889 | B2 | 8/2013 | Efimov et al. |
| 9,849,291 | B2 * | 12/2017 | Keefe .................. A61N 1/3962 |
| 2002/0091414 | A1 | 7/2002 | Bardy et al. |
| 2008/0294210 | A1 | 11/2008 | Rosero |
| 2009/0018599 | A1 | 1/2009 | Hastings et al. |
| 2009/0187227 | A1 | 7/2009 | Palreddy et al. |
| 2009/0198296 | A1 | 8/2009 | Sanghera et al. |
| 2009/0228057 | A1 | 9/2009 | Allavatam et al. |
| 2010/0152798 | A1 | 6/2010 | Sanghera et al. |
| 2010/0152799 | A1 | 6/2010 | Sanghera et al. |
| 2010/0198288 | A1 | 8/2010 | Ostroff |
| 2010/0228308 | A1 | 9/2010 | Cowan et al. |
| 2010/0331904 | A1 | 12/2010 | Warren et al. |
| 2011/0098585 | A1 | 4/2011 | Warren et al. |
| 2011/0098775 | A1 | 4/2011 | Allavatam et al. |
| 2012/0029335 | A1 | 2/2012 | Sudam et al. |
| 2012/0046563 | A1 | 2/2012 | Allavatam et al. |
| 2012/0215269 | A1 | 8/2012 | Tandri et al. |

OTHER PUBLICATIONS

International Application Serial No. PCT/US2012/041633, International Search Report dated Aug. 24, 2012, 3 pgs.
"International Application Serial No. PCT/US2012/041633, Written Opinion dated Aug. 24, 2012", 5 pgs.

* cited by examiner

ANTITACHYCARDIA PACING PULSE FROM A SUBCUTANEOUS DEFIBRILLATOR

RELATED APPLICATIONS

The present application is a continuation of U.S. patent application Ser. No. 13/491,492, filed on Jun. 7, 2012, now U.S. Pat. No. 9,849,291, which claims the benefit of and priority to U.S. Provisional Application No. 61/605,145, filed Feb. 29, 2012, and titled ANTITACHYCARDIA PACING PULSE FROM A SUBCUTANEOUS DEFIBRILLATOR; and claims the benefit of and priority to U.S. Provisional Patent Application No. 61/495,114, filed Jun. 9, 2011, and titled SUBCUTANEOUS SINGLE TERMINATION PULSE THERAPY FOR TACHYARRHYTHMIA, the disclosures of which are incorporated herein by reference.

FIELD

The present invention relates to the field of cardiac rhythm management. More particularly, the present invention relates to ventricular tachyarrhythmia management in implantable therapy systems.

BACKGROUND

Implantable cardiac rhythm management (CRM) systems can be used to help patients susceptible to dangerous high-rate cardiac events. Conventional CRM systems utilize electrodes which are placed in or on the heart for sensing and to pace and shock the heart. The most common such system is a transvenous system, which uses a lead that is threaded through the vasculature and into the heart for attachment in a heart chamber or in a blood vessel of the heart itself. Before the advent of transvenous technology, systems were placed epicardially, with electrodes placed on exterior of the heart in an open-chest surgery. A recent development in the world of CRM systems is the introduction of subcutaneous-only implantable systems, including the S-ICD® system, a subcutaneous implantable defibrillator manufactured by Cameron Health, Inc.

Therapy in CRM systems is often directed at potentially deadly high rate cardiac events. High rate cardiac events may include atrial fibrillation, atrial tachycardia, ventricular fibrillation and/or ventricular tachycardia, among others. Atrial high rate events are often less dangerous and, though possible to treat with implantable systems, are more often pharmacologically mediated. Ventricular high rate events can be more dangerous and are often the target of therapy with implantable devices. Currently two types of therapy for high rate ventricular events are defibrillation and pacing.

Defibrillation is the delivery of high amplitude pulses to the heart, often measured in joules, to correct disorganized rhythms that impair the ability of one or more chambers of the heart to pump blood. The purpose of defibrillation is to depolarize a sufficient mass of the myocardium to allow normal cardiac signals and cycles to resume. If high amplitude therapy is delivered synchronous with a cardiac "beat" in the presence of an atrial tachyarrhythmia, it may be referred to as cardioversion. High energy shocks typically use up to 1000 volts, or more, with durations of up to 30 milliseconds. Total energy for transvenous systems is often in the range of up to 40 Joules, and subcutaneous systems may use up to 80 Joules or more.

A series of high rate pacing stimuli can also be used to treat some tachyarrhythmias. This series of high rate pacing pulses is called Antitachycardia Pacing (ATP). ATP is delivered as a series of pacing pulses by a transvenous or epicardial electrode and can be delivered by an implanted transvenous system in a manner that is not perceptible to the patient, in contrast to defibrillation, which patients notice unless the arrhythmia has rendered them unconscious. In contrast to disorganized arrhythmias that require a defibrillation shock, organized or monomorphic arrhythmias may sometimes be effectively terminated using ATP. Transvenous pacing pulses for ATP typically use up to approximately 7.5 Volts and may have durations up to about 1.5 milliseconds, such that energy levels are well under a single joule. Both pacing and defibrillation can be delivered as monophasic or biphasic waveforms; multiphasic waveforms are known and have been studied but are not particularly common in the field. Subcutaneous systems may use higher energies, for example in the range of up to 40 volts or more; one specific example uses a 200 milliamp constant current biphasic pace pulse with 7.5 milliseconds duration in each phase. While prior discussions of subcutaneous CRM systems have noted the potential applicability of both defibrillation therapy and ATP in subcutaneous CRM systems (see, for example, U.S. Pat. Nos. 6,952,610 and/or 6,856,835) additional or further alternatives are sought.

DETAILED DESCRIPTION

The following detailed description should be read with reference to the drawings. The drawings, which are not necessarily to scale, depict illustrative embodiments and are not intended to limit the scope of the invention. Unless implicitly required or explicitly stated, methods herein do not require any particular order of steps.

Pacing pulses are commonly delivered via an implanted cardiac rhythm management (CRM) system to treat bradycardia and some tachycardia arrhythmias. When a pacing pulse is delivered to positive effect, it is said to "capture" the heart. In order to have capture, the pacing pulse must be delivered to an area of tissue at a point in time that corresponds to an "excitable window," while having at least a requisite amplitude and duration to "excite" the tissue. This excitable window is also known by those skilled in the art as "non-refractory." A local area of cardiac tissue that is effectively stimulated generally causes the adjacent cardiac tissue to depolarize which in turn stimulates further adjacent tissue. This depolarization propagation continues to effectively cause the heart, or a specific chamber of the heart, to contract. A heart beat occurs when the wave of contraction pushes blood out of the heart. Pacing pulses can be used to capture the atria and ventricle(s) independently to accomplish a rhythm that closely resembles normal intrinsic activation of the cardiac muscle.

Anti-tachycardia pacing (ATP) is a method of rapid pacing used in an attempt to terminate rapid tachycardias. ATP can be delivered by transvenous systems in response to certain detected conditions. Generally, ATP is delivered if the cardiac rate is in an elevated, but not extreme zone, for example, in the range of 170-220 beats per minute (bpm), or, alternatively, down to 120 bpm or up to 250 bpm, depending upon the patient, system and settings. If the rate of the arrhythmia is in any of these ranges, it can be termed a tachycardia. If rate (atrial or ventricular) is not driven by normal electrical activation, it may be termed a tachyarrhythmia. A typical use for ATP is to attempt to terminate ventricular tachyarrhythmia (VT). ATP can be delivered at the same or higher amplitude as bradycardia (slow rate) pacing therapy.

VT is generally described in two forms: (1) monomorphic VT (MVT) in which a similar beat-to-beat conduction pattern is noted and (2) polymorphic VT (PVT) in which a varying beat-to-beat conduction pattern or morphology is noted. MVT is generally accepted to be caused by an electrical loop within the cardiac muscle. This electrical loop is commonly referred to as a reentrant circuit by those skilled in the art.

Figure 1:
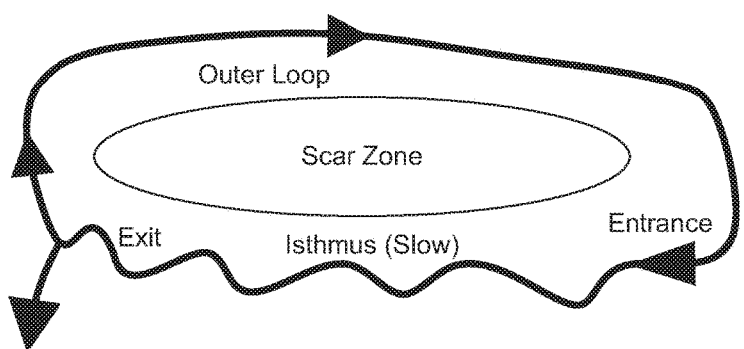
FIG. 1 illustrates the operation of a reentrant circuit which can lead to a ventricular tachycardia.

FIG. 1 is an illustration from O'Donnell et al., from the Indian Pacing and Electrophysiology Journal (2004; 4(2): 63-72), which illustrates the reentrant circuit phenomenon. A region of non-homogenous conduction, for example near a scar (labeled as the "Isthmus" in FIG. 1), provides a slow conduction zone. As electrical activity propagates through tissue, the normal conduction pathway is characterized by repolarized cells that are depolarized by the electrical activity, then enter a refractory state, and repolarize before the next wave of electrical activity arrives. In normal cardiac function, the next wave of electrical activity arrives via the Sino-atrial node, AV node and Purkinje fibers. However, the existence of a slow conduction zone due to scarring of the cardiac substrate (or other cause) can allow a slow moving wave to depolarize tissue in a cyclic fashion. This can create a loop as shown in FIG. 1, in which the electrical wavefront moves slowly through the "Isthmus" and exits into tissue that has had time to repolarize. Depolarization then follows the "Outer Loop" path from the Isthmus "Exit" back to the "Entrance." When the electrical wavefront re-enters the Isthmus, the cycle is able to repeat itself.

Reentry occurs when an electrical impulse enters one side of the reentrant circuit and loops back around the remaining circuit in a continuous manner. When reentry occurs, each iteration of the signal around the circuit causes (localized) depolarization of the cardiac muscle in a manner that is not controlled by the normal conduction system of the heart. Such reentry is often the cause of monomorphic VT. Reentry can lead to undesirable physiological effects at least in part because it is disassociated from the normal conduction system and normal biological controls of cardiac rate. The looping nature of the reentrant arrhythmia can sometimes be terminated by directly stimulating the reentrant circuit in an out-of-sequence manner, thereby disrupting the pattern and terminating the arrhythmia. ATP is one scheme to disrupt the looping electrical activation of the reentrant circuit.

The location of the reentrant circuit relative to the location of the pacing pulse delivered by an endocardial or epicardial electrode can determine the success of reentry termination. If the pacing pulse is delivered far from the reentry circuit the pacing pulse must depolarize, via a wave front, all the cardiac mass between its delivery site and the reentrant circuit before it reaches the reentrant circuit. It is impractical and at times not possible to place the catheter or pacing electrode directly at the site where reentry occurs. Typically multiple pacing pulses called a train or burst are delivered in order to attempt to have one of the pulses reach the reentrant circuit at the critical time needed to interrupt it. Given the uncertain nature and location of this approach, application of a single pacing pulse for ATP is not performed in transvenous systems. Instead, a series of pacing pulses are applied.

The cycle length of the reentrant circuit translates into the rate of the VT. In conventional ATP, the pacing pulses are delivered at intervals shorter than the cycle length of the reentrant circuit in order to overcome the reentrant circuit cycle length. New methods to disrupt the reentrant circuit are desired that will be less reliant on the local propagation of endocardially or epicardially delivered ATP. In addition, given the distant location of subcutaneous electrodes from the reentrant circuit(s) of a VT, new and different approaches are desired for use in a subcutaneous defibrillator.

Post-shock bradycardia pacing is a feature of the S-ICD® system as initially studied and marketed as explained in Bardy et al., AN ENTIRELY SUBCUTANEOUS IMPLANTABLE CARDIOVERTER-DEFIBRILLATOR, N Engl J Med 2010; 363:36-44, Jul. 1, 2010. The delivery of a pacing pulse using only subcutaneous electrodes that do not touch the heart has a less localized effect on the heart than prior conventional transvenous or epicardial pacing systems. This therapy method does not depend upon the heart's internal system of signal propagation for cardiac depolarization, but rather captures the majority of non-refractory, excitable cardiac tissue simultaneously. By delivery of pacing with subcutaneous electrodes, a global capture of the cardiac tissue is achieved. Some external defibrillators may also provide bradycardia pacing, again relying on global capture. The inventors have recognized that this global capture can take away the variability inherent in the proximity-dependence of the transvenous or epicardial approach to ATP.

At any point in the reentrant cycle of a VT, some portion of the reentrant circuit is non-refractory and is therefore excitable—this is a necessary predicate to the reentrant circuit. If an implanted subcutaneous system delivers a pulse across the entire myocardium the non-refractory portion of the reentrant circuit that is driving the VT is excitable and can be reliably stimulated. Thus, rather than a long pulse train of ATP delivered from transvenous or epicardial electrodes, the present invention, in an illustrative example, breaks a reentrant circuit with just one or two pulses delivered by subcutaneous electrodes. This therapy is referred to herein as single termination pulse (STP) therapy which can be delivered subcutaneously, rather than transvenously or epicardially.

Figure 2:
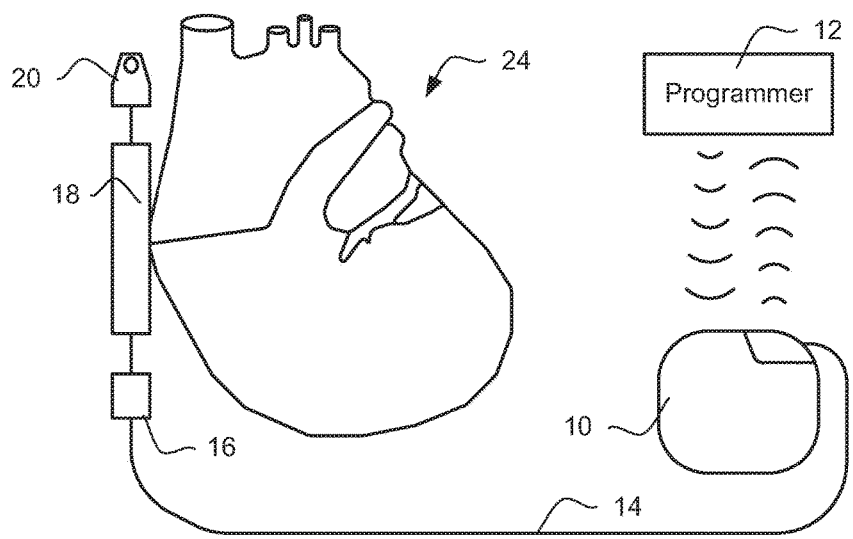
FIG. 2 shows an illustrative placement of a subcutaneous-only CRM system.

FIG. 2 shows an illustrative placement of a subcutaneous-only CRM system. The subcutaneous only system includes a canister 10 configured for communication with a programmer 12, allowing non-invasive programming control and interrogation of the implanted CRM system through use of the programmer 12, using widely known methods and technologies. In addition, the subcutaneous only system canister 10 is coupled to a lead 14 that includes electrodes 16, 18 and 20, all shown disposed in the patient outside of the heart 24. For example, the canister 10 may be at approximately the left axilla, while the lead 14 extends from the left axilla to a line along the sternum, such that electrodes 16, 18 and 20 reside alongside the sternum. Illustrative positions are shown, for example, in U.S. Pat. Nos. 6,647,292, 6,721,597, 7,149,575, 7,194,302, which are incorporated herein by reference, and other locations as well. Subcutaneous placement can include any location between the skin and ribcage, including sub-muscular.

In an example of the present invention, a subcutaneous-only CRM system that has no leads in the venous structure of the patient and no electrodes in or on the heart, is configured to deliver STP therapy in response to an identified tachyarrhythmia. The identified tachyarrhythmia may be of any type, however, in one embodiment the identified tachyarrhythmia may be of a type for which conventional ATP would be delivered in conventional transvenous systems. For example, the identified tachyarrhythmia may be a monomorphic ventricular tachyarrhythmia. In a further example, the subcutaneous-only CRM system may also be configured to deliver defibrillation in response to identified disorganized tachyarrhythmias, bradycardia pacing therapy in response to slow cardiac rhythms (or following defibrillation), and STP, as desired.

In other examples, additional electrodes or leads can be provided, including, in some cases, a transvenous or epicardial lead that will touch the heart. For example, the present described invention can be used in addition to a more conventional transvenous system by adding a subcutaneous electrode for pacing and/or sensing. In such a system, each of conventional ATP, defibrillation, and STP therapy may be available for tachyarrhythmia treatment.

In one example, a conventional pacemaker or a leadless pacemaker (for examples of leadless pacemakers, see US Published Patent Applications 20100198288, 20100228308, 20090018599, 20080294210, among others) may be provided in conjunction with a subcutaneous defibrillator. If multiple implanted systems are provided, the systems may operate cooperatively (for example, through communication between the devices or where one device observes the behavior of another device and adjusts its own response accordingly) or independently.

Figure 3:
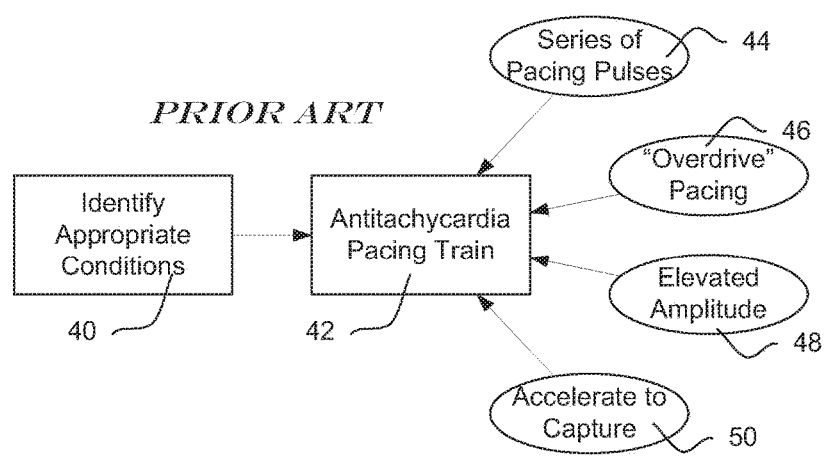
FIG. 3 provides an illustration of an anti-tachycardia pacing (ATP) method.

FIG. 3 provides an illustration of conventional ATP. Generally the process of the prior art shown in FIG. 3 includes identifying appropriate conditions for delivering ATP, as shown at 40. Typically this would include identification of an elevated, but not extreme, rate, for example, above 120 bpm, up to somewhere in the range of 250 bpm, depending on patient age and physician preference. ATP rate boundaries may be programmable.

Once conditions are correct at 40, a conventional ATP pulse train is delivered as noted at 42. ATP typically includes delivery of a train of pulses, as noted at 44, and is often termed "overdrive" pacing 46. ATP may be delivered at an elevated amplitude (which is optional) relative to that required for a given patient for bradycardia pacing, as noted at 48. ATP can also be applied using a rate that is a percentage of the observed rate of the tachycardia. The rate of the pacing train may be accelerated over time, from a first rate to a second rate, with the second rate being above the detected tachyarrhythmia rate, as noted at 50. Thus, the heart is accelerated to a rate above the rate defined by the ventricular tachyarrhythmia during ATP, in order to capture and terminate the reentrant circuit. The timing of the pacing pulse may be important to the successful termination of VT. It may be necessary for the ATP to either be synchronous to the QRS or offset at a number of milliseconds from sensing of the QRS. The offset could also be calculated as a percentage of the cycle length of the VT.

Figure 4:
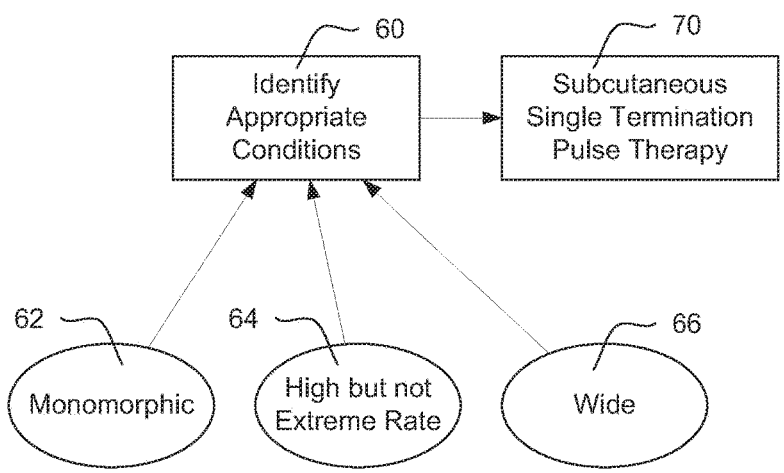
FIG. 4 provides an illustration of a subcutaneous single termination pulse method.

FIG. 4 provides an illustration of STP therapy for tachyarrhythmia. In the illustrative method, appropriate conditions 60 for the STP therapy can include a monomorphic signal 62, rate in an elevated but not extreme range 64 (such as 120-250 bpm with narrower, higher or lower ranges possible if preferred), and, optionally, a wide signal 66. Other conditions may also apply, and one or more of 62 or 66 may be omitted, if desired. Identification of a monomorphic signal 62 can include correlation analysis to a template or between detected events, using, for example, correlation waveform analysis, wavelet transform, principal components analysis, amplitude and/or width. One important distinction is that the STP therapy is delivered at a much lower amplitude than defibrillation therapy. The amplitudes of different therapies in a single system are best understood as grouped together because the same therapies in different systems may be delivered at very different amplitudes. Thus, for example, illustrative systems may be as follows:

System 1: STP at 15 ms (biphasic signal with two 7.5 ms phases) at 200 mA constant current across a range of 25-400 ohms gives 15 mJ to 240 mJ; Defibrillation at 80 Joules (biphasic truncated exponential)—thus the delivered energy for defibrillation in System 1 (which may be implanted as shown in FIG. 2) is at least two orders of magnitude greater than the delivered energy for the STP; for such a system the voltage of STP is between 5-80 volts (constant current yields a range of delivered voltage) while the voltage of the defibrillation begins at 1350 V and decays during defibrillation to about 340 volts.

System 2: STP at 12 ms (biphasic signal with two 6 ms phases) at 20 V constant voltage across a range of 20-350 ohms gives delivered energy of 17 mJ to 240 mJ and Defibrillation at 60 Joules (Biphasic truncated exponential again) provides another system in which at least two orders of magnitude separate the delivered energy of defibrillation from the delivered energy of STP.

System 3: STP at 10 ms (biphasic signal with two 5 ms phases) at 120 mA constant current across a range of 20-300 ohms gives 3 mJ up to 43 mJ, and Defibrillation at 40 Joules (biphasic truncated exponential) provides another system in which at least two orders of magnitude separate the delivered energy of defibrillation from the delivered energy of STP System 4: STP at 60 ms (monophasic signal) at 120 mA constant current across a range of 25-400 ohms gives 22 mJ to 346 mJ; Defibrillation at 70 Joules again provides a system in which at least two orders of magnitude separate the delivered energy of defibrillation from the delivered energy of STP.

In each of Illustrative Systems 1-4, ATP may be delivered as well by using a pulse train as described above. Depending on system configuration, ATP could be delivered using the same waveform and amplitude as STP (for example, if all electrodes are subcutaneous only), or ATP could be delivered at lower amplitudes (for example, if ATP is locally delivered by using electrodes attached to the myocardium, and STP is delivered globally using far-field electrodes) than STP. A pulse train length for ATP may be programmable; for example, some commercially available systems are programmable between 8-28 pulses.

Once conditions are appropriate at 60, STP therapy is delivered at 70. In some examples, the STP therapy is delivered using only subcutaneous electrodes, in order to deliver the therapy across the entire myocardium and impact whichever part of the reentrant path is excitable at the time STP therapy is delivered. Various amplitudes and signal types may apply instead, for example:

Constant, ramped or declining currents of 25-250 milliamps with durations of about 1-80 ms per phase;

Monophasic or biphasic waveforms;

Constant, ramped or declining voltages of 5-300 volts; or

Predetermined waveforms delivering a particular amount of energy, from 0.01 Joules to 5 Joules, for example. Some particular examples include, for example:

Delivering biphasic constant voltage pulse having an output of about 25-125 volts and a duration of from 1 to 20 milliseconds;

Delivering a truncated exponentially decaying voltage output having an initial voltage of about 50-125 volts, duration of from 1 to 20 milliseconds with an output capacitance of about 50-125 microfarads Delivering a monophasic constant current pulse having an output of 120 mA and a duration of 40-70 milliseconds; and Delivering a biphasic constant current pulse having a current of about 200 mA and pulse width of about 7.5 milliseconds per phase.

As described in Bardy et al. in the New England Journal of Medicine, the pulse generator of the S-ICD® system from Cameron Health is configured to deliver pacing pulses with a constant current output of 200 mA, as a biphasic 7.5 mS per phase signal. This is, for the system implant location represented by FIG. 2, sufficient to capture the entire myocardium for most patients. This output may be used for either bradycardia pacing or for STP. Lesser or greater output currents may be used. If desired, capture testing maybe performed by delivering pacing pulses via electrodes that are remote from the heart by applying different signal amplitudes or pulse-widths. Capture testing may be performed at the implant of a system and/or at periodic (such as at semi-annual follow-up visits) or occasional (i.e. after an event takes place) times, if desired.

It is common for pacing pulses delivered to subcutaneous electrodes to cause skeletal muscle contraction. This may or may not be uncomfortable to the patient. It may be reasonable to demonstrate to the patient what pacing would feel like so they could be prepared for the sensation. Such demonstrations could be performed in a clinical environment. It would be also be possible to have an implantable system automatically perform such testing and/or to perform capture threshold testing under remote follow-up control.

Other waveforms and shapes can be used, including multiphasic therapies having more than two phases, or using more than two electrodes in any suitable configuration. Monophasic therapy may be delivered as well, as well as pulse widths out to 60 milliseconds, with the longer pulse widths potentially reducing skeletal muscle activation. STP therapy is different from defibrillation or cardioversion therapy in that the output is much smaller in energy level (often less than a Joule of energy), and is different from ATP and other pacing therapy in that only one pulse is delivered, rather than a train of pulses intended to cause the heart to reach or exceed a predetermined rate. In an additional embodiment, two pulses are delivered for STP. For purposes of this disclosure, STP and ATP are distinguished from one another by the following rules:

delivery of a train of pulses greater than four, without intervening assessment between pulses of the success of a previous pulse, is considered an ATP train;

delivery of one or more sets of 1-4 pulses separated by assessment of the success of the previous pulses, is considered STP. In these examples, each pulse may take the form of a monophasic, biphasic, or otherphasic waveform, with constant or exponential decaying current or voltage, or other suitable shape (such as rounded or ramped, as have been disclosed elsewhere in the art).

In some examples, a single STP therapy will be all that is delivered. In one embodiment, if a first delivery fails to terminate a ventricular tachycardia, a second therapy of the same or higher amplitude may be provided. In another embodiment, if the single STP therapy fails to terminate the ventricular tachycardia, two STP therapies may be provided at some interval. The interval between multiple therapies may be predetermined, for example, in the range of 300-600 milliseconds. In some embodiments the interval between multiple therapies may be based on a combination of factors including, for example, selecting an interval associated with the observed rate of tachycardia (i.e., if the rate of tachycardia is 200 bpm, the tachycardia interval would be 333 milliseconds, and a shorter interval can be used as the interval between STP therapies). An additional factor may be the avoidance of T-waves, such that the interval between therapies is selected to ensure that the multiple STP therapies delivered in succession do not land of the T-wave if the heart is not captured by the first such therapy delivery. In one embodiment, a sequence of STP may be delivered leading, ultimately, to defibrillation therapy if no STP therapy succeeds. For example, single therapy delivery may be followed by a pair of STP therapy deliveries, followed by three STP therapy deliveries, and, if none of these tiers of STP therapy succeeds, a defibrillation therapy is delivered.

In the context of STP, one factor to consider is the timing of the pacing pulse delivery. To enhance the effectiveness, the STP therapy may be delivered either synchronized with or offset by a few milliseconds from the peak of a QRS signal. Synchrony may be accomplished by using a detection method that relies on identifying the onset of a QRS and choosing a point in time in the middle of the QRS. If desired, the width of the R-wave may be estimated and used as the delay from detection to delivery within a QRS. In another example, if intervals are regular (generally a precondition to delivery of STP or ATP), the system can predict when to most effectively deliver the STP signal by observation of the R-wave peak in previous signals. An offset from QRS sensing can also be calculated using a percentage of the cycle length of the observed tachycardia.

In another embodiment, STP may be suppressed in the presence of signals that suggest a potential for inappropriate timing of the STP delivery. In particular, delivery of stimulus pulses on top of the cardiac "T-wave" has been known to be pro-arrhythmic and can initiate ventricular fibrillation. To avoid such delivery, one or more conditions may be required. In one embodiment, a ratio of the height of the T-wave to the R-wave for the captured cardiac signal may be estimated and, if the ratio of the T-wave to the R-wave exceeds some amount (for example, 50-75% could be the maximum allowable ratio), then STP will not be delivered. In another embodiment, avoidance of STP-on-the-T-wave may be accomplished by observing the regularity of intervals in the signal and, when STP is to be delivered, ensuring that the STP is delivered after an interval that is similar to other intervals (i.e. between 80% and 100% of the preceding interval average). For this latter method, an additional requirement may include assessment of the morphology of the detections that give rise to the measured intervals to ensure that such detections are not the cardiac T-wave. Width or correlation analysis, for example, can be used.

It may be noted that a train of pacing pulses can be used to make induction easier when using a shock-on-T approach. Pacing the heart at a rate higher than the sinus rate and then timing the shock-on-T to intentionally land on the nadir of the T wave may be used to induce VF. If the energy level of the successfully delivered defibrillation shock is below the maximum output of the S-ICD then a safety margin is obtained. By applying a pulse train, and narrowing the stimulus intervals over time, one can make it easier to predict the timing of the T-wave.

Figure 5:
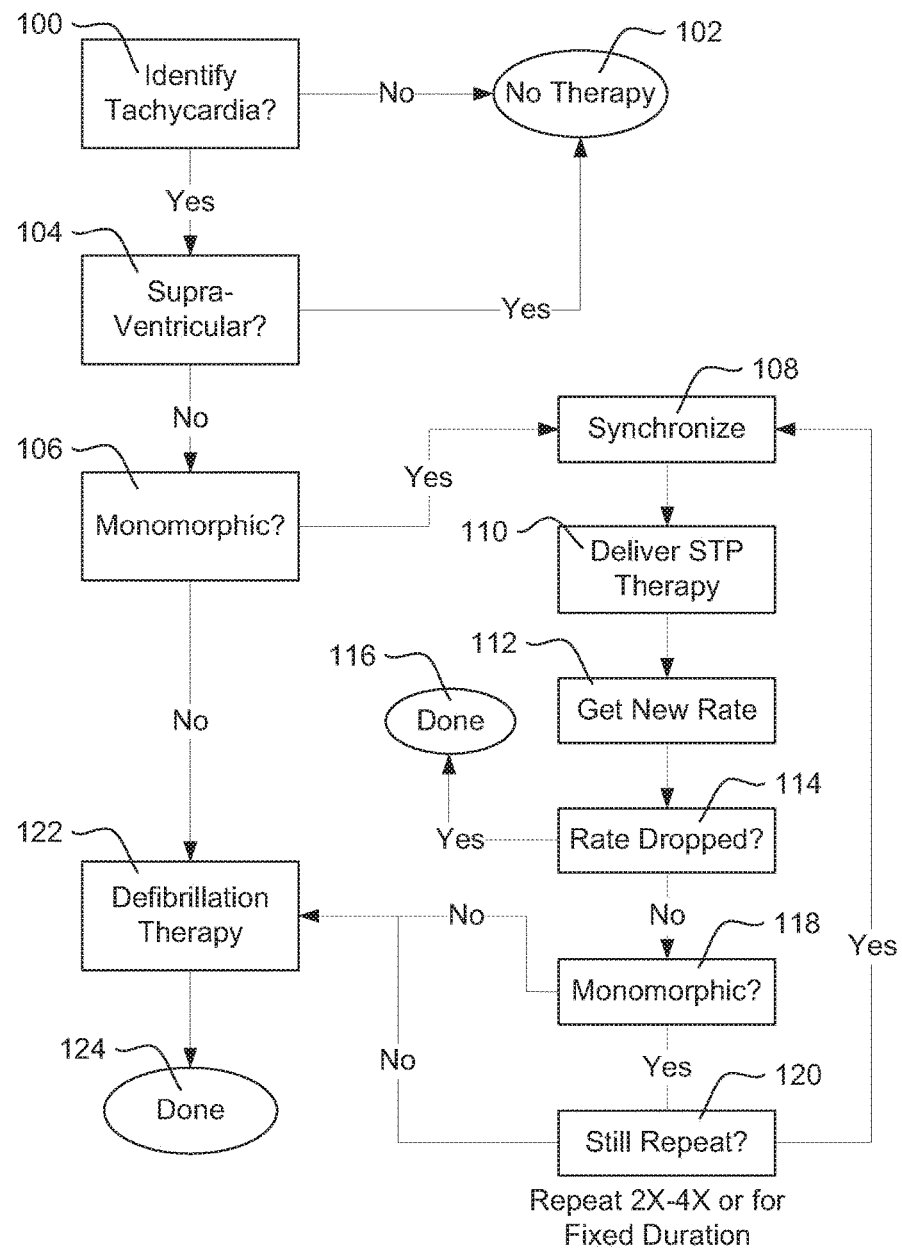
FIG. 5 provides an illustration of a patient treatment method.

FIG. 5 provides an illustration of a patient treatment method. The illustrative method begins with a determination of whether there is a tachycardia at 100. Any high rate condition may be sought, for example, rate above a threshold set in the range of 120 to 220 beats per minute. If there is no tachycardia, no tachy-related therapy is needed and the method stops at 102.

If a tachycardia is occurring, the next step is to determine whether the tachycardia is supraventricular in origin. This may be determined by numerous processes depending upon the system. A dual chamber transvenous system could answer the query at 104 by comparing atrial and ventricular detections, for example. An implantable system could look at morphology using a template, for example, of normal sinus rhythm; finding similarity to the template would indicate a supraventricular rhythm. Width may also be used as an indicator, with narrower morphology suggesting supraventricular origin. If the tachycardia is supraventricular, again, no therapy is delivered an the method stops at 102. In an alternative, if a supraventricular tachycardia is occurring, analysis may be performed to determine whether an atrial arrhythmia conducive to therapy is occurring.

If the tachycardia is not supraventricular, the device may declare a treatable episode of tachycardia is occurring. Episode declaration may trigger advanced functionality in the device to operate (such as high voltage circuitry and additional processing circuitry), and may cause the device to store data related to the episode for later physician assessment. The next step is to determine whether the tachycardia is monomorphic, as shown at 106. A monomorphic tachycardia can be identified by several markers, for example, by comparing the shape or width of one beat to one or more previous beats (if each is similar, it is monomorphic), by observing amplitude, frequency content, wavelet transform, or by other analyses known in the art. If a monomorphic tachycardia is occurring, then the system concludes that a pace-terminable VT may be taking place, and a STP therapy regimen is entered. The initial therapy is delivered by synchronizing to avoid a T-wave (if any is occurring) as shown at 108, followed by a set of STP being delivered, as shown at 110. The number of pulses to deliver in an STP set may be programmable or it may be preset.

Next, the cardiac rate is measured following therapy delivery, as shown at 112; this may require waiting for the next 4-12 heart beats to be observed. Once a new rate is obtained, the method includes determining whether the rate has dropped following pacing delivery, as shown at 114. The method terminates at 116 if the rate has dropped in response to the pacing therapy, and this may be considered a success. When done at 116, data may be recorded to the pulse generator memory and any other suitable functions may be performed, as known to those skilled in the art.

If the rate has not dropped at block 116, the method includes determining whether the observed signal continues to be monomorphic, as shown at 118, which can be assessed in similar fashion to block 106. If the observed signal is no longer monomorphic at 118, given that the rate has not dropped at 114 as well, the system proceeds to deliver defibrillation therapy as shown at 122. If the signal is still monomorphic at 118, the method includes determining whether it may repeat the STP process as shown at 120. As noted, this sequence may be repeated two to four times or, alternatively, for a fixed period of time such as up to 30 seconds. In other examples, there may be no repetition or, alternatively, more than four repetitions or longer durations may be applied. If there are still allowable repetitions at block 120, the method loops back to block 108. The method may be performed as a "pacing while charging" approach (similar to ATP while charging), and repetition may continue until the capacitors used for high energy defibrillation therapy are fully charged. In an example, a system may go through the STP loop once before beginning high voltage therapy preparations by charging the capacitors. If no further repetitions are allowed at block 120, the method continues to block 122 for defibrillation therapy delivery.

Going back to block 106, if a polymorphic arrhythmia has been observed, that is, the signal is not monomorphic, the method can proceed directly to block 122 and defibrillation therapy. After defibrillation therapy is delivered, the method ends as noted at block 124. As noted above, the delivery of defibrillation therapy at block 122 may include defibrillation itself plus delivery of post-shock bradycardia pacing, if desired and needed.

In another embodiment, a transvenous system may be used to perform STP using only its far-field electrodes. Specifically, the defibrillation coil(s) may be used as one pole of the STP delivery, with the canister (typically implanted in a subclavicular or high-pectoral position) serving as the other pole. Though not as readily "global" as a purely subcutaneous system, this approach may be used as well. The STP may be integrated into a tiered therapy system in either of two ways: ATP first, STP second, and defibrillation third, or STP first, ATP second, and defibrillation third. In such a system, the ATP may be delivered using pacing electrodes at the tip of the transvenous lead, with the STP delivered using a different set of electrodes. Further, while ATP may be delivered using conventional energy levels and pulse widths, the STP delivery may be at higher voltage and/or duration (for example, ATP at 5 volts with 0.5 to 1.5 ms duration, and STP at 5-20 volts and 2-80 ms duration). The STP delivery would follow the same approach as shown in FIG. 5, but with addition of ATP as another part of the therapy chain either before or after STP.

In a separate embodiment, the delivery of pacing therapy directly on the T-wave can be used to establish the upper limit of vulnerability. An approach used in transvenous systems includes delivering a larger amplitude pulse on the T-wave to determine whether the shock on T induces VF. When the pulse amplitude is above the upper limit of vulnerability, no VF will be induced. When the pulse amplitude becomes low enough, VF is induced. The result is an estimation of the amplitude needed for defibrillation—the defibrillation threshold is going to be defined near the upper limit of vulnerability. This approach may be used in a subcutaneous system as well as in in a transvenous system.

Various additional details for, further features of, or alternatives to the system of FIG. 1, can be found in the disclosures of the following patents and patent applications, which are incorporated herein by reference as showing further illustrative examples of implantable medical device systems/components, methods of their use, and accessories: U.S. Pat. Nos. 6,647,292, 6,721,597, 6,754,528, 6,865,417, 6,937,907, 6,952,608, 6,954,670, 7,065,407, 7,120,495, 7,149,575, 7,194,302, 7,248,921, 7,330,757, 7,359,754, 7,376,458, 7,392,085, 7,477,935, 7,555,338, 7,623,909, 7,623,913, 7,623,916, 7,655,014, 7,769,457, 7,962,212, 8,079,959, 8,160,686, and 8,160,687; US Pub. Pat. Apps. 2009-0187227, 2009-0198296, 2009-0228057, 2010-0152798, 2010-0152799, 2010-0331904, 2011-0098585, 2011-0098775, 2012-0029335, and 2012-0046563. The present invention is not limited to any of the particular examples shown in these commonly assigned patents or applications, and numerous alternatives will be recognized by those skilled in the art.

Referring briefly to FIG. 2, the canister 10 may include an electrode that can be a discrete electrode, a portion of the surface of the canister 10, or may be the entire surface of the canister 10. The canister 10 preferably contains operational circuitry for the system. The operational circuitry may include a controller, microcontroller or microprocessor, and any suitable analog and/or digital circuits needed for signal processing, memory storage and generation of high-power, low-power electrical or non-electrical outputs. The operational circuitry may be coupled to suitable battery technology for an implantable device, with any of numerous examples well known in the art, and may use various capacitor technologies to assist in the short term build-up and/or storage of energy for defibrillation or other high output purposes. The lead 14 and external shell for the canister 10 can be manufactured with various materials suitable for implantation, such as those widely known, along with coatings for such materials, throughout the art. For example, the canister can be made using titanium, with a titanium nitride or iridium oxide (or other material) coating if desired, and the lead can be formed with a polymeric material such as a polyether, polyester, polyamide, polyurethane or polycarbonate, or other material such as silicon rubber. The electrodes 16, 18 and/or 20 can be formed of suitable materials as well, such as silver, gold, titanium or stainless steel such as MP35N stainless steel alloy, or other materials.

In one illustrative example, a subcutaneous defibrillator and a leadless pacing system operably function cooperatively by having a master controller configured to instruct the operations of defibrillation circuitry and pacing modules. In such an example, the master controller is configured to allow ATP to be ordered from the leadless pacing system, STP to be ordered from the subcutaneous defibrillator, and defibrillation to be ordered from the subcutaneous defibrillator. Further in the example, the master controller is configured to order ATP first in response to a monomorphic VT; if the rhythm does not convert, the master controller next orders STP; if the rhythm still fails to convert, the master controller next orders defibrillation therapy. If ATP is delivered and is not successful, the master controller will then store a template of the monomorphic VT and, if/when the template is again matched in the future, the ATP will be skipped.

In another illustrative example, a subcutaneous defibrillator and a transvenous pacemaker can operably function cooperatively together. One of the subcutaneous defibrillator or the transvenous pacemaker may be designated as the master controller for the implanted systems, such that the master controller controls both implanted systems. Specifically, the master controller can order ATP from the transvenous pacemaker and can order STP and defibrillation from the subcutaneous defibrillator. Further in the example, the master controller is configured to order ATP first in response to a monomorphic VT; if the rhythm does not convert, the master controller next orders STP; if the rhythm still fails to convert, the master controller next orders defibrillation therapy. If ATP is delivered and is not successful, the master controller will then store a template of the monomorphic VT and, if/when the template is again matched in the future, the ATP will be skipped.

In yet another illustrative example, a system comprises a transvenous lead and a subcutaneous lead, as well as an active canister. The system is configured for ATP delivery using a tip electrode and ring electrode both on the transvenous lead. The system is further configured for STP therapy delivery using one or more combinations of the subcutaneous electrode, the canister, and, if desired, a coil electrode on the transvenous lead. Finally, the system is configured for defibrillation therapy using the canister, coil electrode and/or subcutaneous electrode. In one embodiment, no coil electrode is provided on the transvenous lead, allowing a less complex lead to be provided. For an embodiment lacking a transvenous coil electrode, the STP and defibrillation delivery configurations would use only the subcutaneous lead and the canister.

Those skilled in the art will recognize that the present invention may be manifested in a variety of forms other than the specific embodiments described and contemplated herein. Accordingly, departures in form and detail may be made without departing from the scope of the present invention.

What is claimed is:

1. A method of treating a patient in an implantable cardiac rhythm management device (CRMD) comprising a canister housing circuitry for performing data analysis and therapy delivery, coupled to a lead electrode having electrodes for body implantation suitable for sensing electrical signals, the method comprising:
   receiving cardiac signals from the patient using one or more of the electrodes on the lead;
   identifying that a tachycardia is occurring based on the received cardiac signals showing a cardiac rate in excess of a rate threshold;
   determining that the tachycardia is not supraventricular in nature and declaring a treatable episode of tachycardia;
   determining that the tachycardia is monomorphic;
   delivering synchronized pacing pulses to the patient using far-field electrodes in response to the monomorphic tachycardia;
   calculating the cardiac rate of the patient following the delivery of the synchronized pacing pulses;
   determining that the cardiac rate dropped in response to the synchronized pacing pulses; and
   terminating the episode and storing data related to the episode.

2. The method of claim 1 wherein the CRMD is a subcutaneous-only CRMD and the far-field electrodes used for therapy delivery are subcutaneously placed electrodes.

3. The method of claim 1 wherein the CRMD is a transvenous CRMD having at least one transvenous lead, and the far-field electrodes used for therapy delivery include a transvenous coil electrode and an electrode disposed on the canister.

4. The method of claim 1 wherein the rate threshold is in the range of 120-220 beats per minute.

5. The method of claim 1 wherein the CRMD determines that the tachycardia is not supraventricular in nature by determining that the detected cardiac signals comprise a wide morphology.

6. The method of claim 1 wherein the CRMD determines that the tachycardia is not supraventricular in nature by determining that the detected cardiac signals do not match a template of normal sinus rhythm.

7. The method of claim 1 wherein the CRMD determines that the tachycardia is not supraventricular in nature by comparing atrial and ventricular detections.

8. The method of claim 1 wherein the CRMD determines that the tachycardia is monomorphic by comparing the shape of one detected cardiac beat to one or more previous detected cardiac beats.

9. The method of claim 1 wherein the CRMD determines that the tachycardia is monomorphic by comparing the width of one detected cardiac beat to one or more previous detected cardiac beats.

10. An implantable cardiac rhythm management device (CRMD) comprising a canister housing operational circuitry for performing data analysis and therapy delivery, coupled to a lead electrode assembly having electrodes for body implantation suitable for sensing electrical signals, wherein the operational circuitry is configured to perform a method comprising:

the operational circuitry receiving cardiac signals from the patient using one or more of the electrodes on the lead;

the operational circuitry identifying that a tachycardia is occurring based on the received cardiac signals showing a cardiac rate in excess of a rate threshold;

the operational circuitry determining that the tachycardia is not supraventricular in nature and declaring a treatable episode of tachycardia;

the operational circuitry determining that the tachycardia is monomorphic;

the operational circuitry delivering synchronized pacing pulses to the patient using far-field electrodes on the lead electrode assembly and/or canister in response to the monomorphic tachycardia;

the operational circuitry calculating the cardiac rate of the patient following the delivery of the synchronized pacing pulses;

the operational circuitry determining whether the cardiac rate dropped in response to the synchronized pacing pulses; and in response to determining that the cardiac rate dropped in response to the synchronized pacing pulses, the operational circuitry terminating the episode and storing data related to the episode in memory.

11. The CRMD of claim 10 wherein the CRMD is a subcutaneous-only CRMD and the lead electrode assembly is designed for subcutaneous placement, such that the far-field electrodes are designed for subcutaneous placement.

12. The CRMD of claim 10 wherein the CRMD is a transvenous CRMD and the lead electrode assembly is configured for transvenous placement and includes a coil electrode such that far-field electrodes used for therapy delivery include the coil electrode and an electrode disposed on the canister.

13. The CRMD of claim 10 wherein the operational circuitry is configured such that the rate threshold is in the range of 120-220 beats per minute.

14. The CRMD of claim 10 wherein the method that the operational circuitry is configured to perform further comprises, in response to determining that the cardiac rate did not drop in response to the synchronized pacing pulses, the operational circuitry preparing for and delivering defibrillation therapy to the patient using the far field electrodes.

15. The CRMD of claim 10 wherein the operational circuitry is configured to determine that the tachycardia is not supraventricular in nature by determining that the detected cardiac signals comprise a wide morphology.

16. The CRMD of claim 10 wherein the operational circuitry is configured to determine that the tachycardia is not supraventricular in nature by determining that the detected cardiac signals do not match a template of normal sinus rhythm.

17. The CRMD of claim 10 wherein the operational circuitry is configured to determine that the tachycardia is not supraventricular in nature by comparing atrial and ventricular detections.

18. The CRMD of claim 10 wherein the operational circuitry is configured to determine that the tachycardia is monomorphic by comparing the shape of one detected cardiac beat to one or more previous detected cardiac beats.

19. The CRMD of claim 10 wherein the operational circuitry is configured to determine that the tachycardia is monomorphic by comparing the width of one detected cardiac beat to one or more previous detected cardiac beats.

20. A method of treating a patient in an implantable cardiac rhythm management device (CRMD) comprising a canister housing circuitry for performing data analysis and therapy delivery, coupled to a lead electrode having electrodes for body implantation suitable for sensing electrical signals, the method comprising:

receiving cardiac signals from the patient using one or more of the electrodes on the lead;

identifying that a tachycardia is occurring based on the received cardiac signals showing a cardiac rate in excess of a rate threshold;

determining that the tachycardia is not supraventricular in nature and declaring a treatable episode of tachycardia;

determining that the tachycardia is monomorphic;

(a) delivering synchronized pacing pulses to the patient using far-field electrodes in response to the monomorphic tachycardia;

(b) calculating the cardiac rate of the patient following (a);

(c) determining that the cardiac rate calculated at (b) did not drop;

(d) in response to (c), determining whether the tachycardia remains monomorphic following (a), and:

if the tachycardia remains monomorphic, returning to (a) up to a predetermined quantity of iterations, or if the tachycardia is no longer monomorphic or the predetermined quantity of iterations has already taken place, preparing for and delivering defibrillation therapy.

* * * * *